United States Patent [19]
Sawai et al.

[11] Patent Number: 5,625,153
[45] Date of Patent: Apr. 29, 1997

[54] METHOD OF NON-DESTRUCTIVELY ESTIMATING LIFE OF CERAMIC MEMBER

[75] Inventors: Yuichi Sawai, Hitachi; Yoshiyuki Yasutomi, Mito; Motoyuki Miyata, Hitachi; Hideki Tamaki, Hitachi; Katsuo Wada, Hitachi, all of Japan

[73] Assignee: Hitachi, Ltd., Tokyo, Japan

[21] Appl. No.: 572,891

[22] Filed: Dec. 18, 1995

[30] Foreign Application Priority Data

Dec. 19, 1994 [JP] Japan .................................. 6-314873

[51] Int. Cl.⁶ ......................................................... G01N 3/00
[52] U.S. Cl. ................................................................. 73/762
[58] Field of Search .............................. 73/116, 762, 787, 73/800, 802, 799; 376/249

[56] References Cited

U.S. PATENT DOCUMENTS

| | | |
|---|---|---|
| 3,779,071 | 12/1973 | Thomas, Jr. et al. . |
| 4,015,465 | 4/1977 | Scott ........................................... 73/762 |
| 4,465,900 | 8/1984 | Mitsumatsu et al. . |
| 4,768,383 | 9/1988 | Koyama et al. ............................ 73/787 |

*Primary Examiner*—Robert Raevis
*Attorney, Agent, or Firm*—Antonelli, Terry, Stout & Kraus, LLP

[57] ABSTRACT

A method of estimating non-destructively the life expectancy of ceramic members, at least a surface layer of which is made of ceramics, is disclosed. The method comprises measuring a variation in at least one of physical characteristics of said ceramic members including color, grain size, electroconductivity and Young's modulus and estimating the life expectancy of the ceramic members on the basis of the predetermined relationship between the life of said ceramics and the physical characteristics. The method is excellent in estimation of the life expectancy of ceramic members of gas turbines or nuclear fusion reactor since the life expectancy of the members to be inspected can easily be estimated in a short time without fracturing the members.

22 Claims, 8 Drawing Sheets

DIRECTION OF DIFFUSION OF COLOR DEVELOPER ELEMENT

METHOD OF NON-DESTRUCTIVELY ESTIMATING LIFE OF CERAMIC MEMBER

BACKGROUND OF THE INVENTION

1. Field of the Invention

The present invention relates to a method of non-destructively inspecting ceramic members such as gas turbine blades, burners, walls flame sprayed with ceramics for a nuclear fusion reactor, tiles of a space shuttle, and the like to estimate the life expectancy of the members.

2. Description of the Related Art

An attempt has been made to make gas turbines workable at higher temperatures in order to improve the electricity generation efficiency of the gas turbines. Such increase in temperature requires a member having a higher thermal resistance and there have been utilized gas turbine members having an adiabatic layer flame sprayed with ceramics.

It is necessary to know the life of these gas turbine members, for example, gas turbine blades and it is also desired that the inspection of the members for determining the life expectancy thereof be accomplished at a lower cost as well as in a possibly shortest break down time of the gas turbines. The estimation of the life of turbine blades has been made heretofore by cutting off a part of the ceramic coating layer formed on the gas turbine blades by a flame spraying method and directly inspecting the grain growth of the surface layer of the heat resistant metal substrate.

The prior art inspection as above suffers from the necessity for fracturing partly ceramic members such as turbine blades every time when the periodical inspection is effected and the considerably long time required for the inspection to be completed. In addition to the problem that the ceramic coating layer must be removed out of the turbine blade substrate, there has not been established a method of predicting the expected life to the time when actual release of the coatings occurs. Moreover, there is a problem that the conventional inspection process will not be able to apply when the whole turbine blade becomes made of ceramics in future.

SUMMARY OF THE INVENTION

With respect to the prediction of the life of ceramic members as described above, an object of the present invention is to provide a method of estimating the life expectancy of a ceramic member by a non-destructive inspection in a short time.

DETAILED DESCRIPTION OF PREFERRED EMBODIMENTS

In an embodiment to achieve the above purposes, the present invention is to non-destructively estimate the life expectancy of ceramic members by measuring the variation in physical properties of the ceramic members owing to growth of ceramic grains and diffusion of foreign elements into the ceramics.

The ceramic members may deteriorate due to thermal history and produce cracks. Particularly, ceramic coating layers coated on the surfaces of metal substrates may come to release in accordance with the thermal history.

The roughening of the texture of ceramics due to the grain growth may cause a reduction in strength of the ceramics reaching a critical grain size at which the ceramics become quite easy to fracture. This critical grain size varies depending upon the type of ceramic.

The physical quantities which vary in accordance with the growth of ceramic grain and the diffusion of foreign elements into the ceramics relates closely to the thermal history.

In the present invention the relationship between the physical quantities depending upon the thermal history and the life of the ceramic members is predetermined. The ceramic members are evaluated for the variation in the physical quantities is measured and estimated for the life expectancy with reference to the relationship.

If the ceramic members are colored, the color varies with the growth of grain enabling to estimate the life expectancy. In the case of $ZrO_2$, an addition of element(s) such as V, In, or Y+V allows the ceramic grains to be colored. In the case of $ZrSiO_4$ ceramics, an addition of Co+Ni provides a gray color to the ceramics, CdS or Pr a yellow color, Fe a pink color, and V a blue color. In the case of $SnO_2$ ceramics, an addition of V or Ti provides a yellow color, Sb a gray color, and Cr a pink color. In the case of $TiO_2$ ceramics, an addition of Cr+Sb or W+Sb provides a yellow color. In the case of $\alpha-Al_2O_3$ ceramics, an addition of Mn or P provides a pink color and Cr a green color. In the case of highly pure SiC ceramics, an addition of N+P provides a green color to the ceramics and B+Al a green color.

The colors of the members made of these colored ceramics vary with the size of ceramic grain, so that the variation in color corresponding to the growth of grain in the ceramic members allows estimating the life expectancy thereof.

Reference may be made to JIS-Z-8721 for color designation as follows: a yellow color may be expressed by a combination of H, V and C values selected from H=10 YR, 2.5 Y, 5 Y, 7.5 Y, or 10 Y; V=3 to 8; and C=1 to 16: a blue color may be expressed by a combination of H, V and C values selected from H=10 BG, 2.5 B, 5 B, 7.5 B, or 10 B; V=3 to 8; and C=1 to 16: a green color may be expressed by a combination of H, V and C values selected from H=10GY, 2.5 G, 5 G, 7.5 G, or 10 G; V=3 to 8; and C=1 to 16: a pink color may be expressed by a combination of H, V and C values selected from H=5 R, 2.5 R, 10 RP, 7.5 RP, or 5 RP; V=3 to 8; and C=1 to 16: a gray color may be expressed by any one of N3, N5, or N7.

The coloration may be made simply by adding to at least a part of the materials for a ceramic, or coating on a ceramic member, compound(s) containing a color developer element capable of developing a desired color. As the ceramic is subjected to thermal conditions, the color developer element (s) will diffuse into the ceramic and react or form a solid solution depending upon the thermal history to change the color of the ceramic which allows estimation of the life expectancy of the ceramic.

Alternatively, the coloration may be made simply by adding to or coating on the ceramics compound(s) containing two or more developer elements capable of developing desired color(s). As the ceramic is subjected to thermal conditions, the color developer elements will diffuse into the ceramic at a respective diffusion rate and react or form a solid solution depending upon thermal history to change the color of the ceramic depending upon the period of operation time which allows estimation of the life expectancy of the ceramic.

Ceramics, the life expectancy of which may be estimated by the present method, include AlN, $Al_2O_3$, $Al_6Si_2O_{13}$, $B_4O$, $Bi_2O_3$, BN, $BaTiO_3$, CrC, $Cr_3C_2$, $Cr_2O_3$, $CrO_2$, CoO, $Fe_3O_4$, MnO, MgO, NiO, $Si_3N_4$, SiC, SiAlON, $SnO_2$, $TiB_2$, TiN, TiC, $TiO_2$, $Ti_2O_5$, $Ti_2O_3$, $ZrB_2ZrO_2$, $ZrSiO_4$, and a combination of two or more thereof.

Electroconductive or semiconductive ceramic members vary in electroconductivity with the growth of grain according to the thermal history which also allows estimation of the life estimation. Ceramic members, the life expectancy of which may be estimated by such method, include those made any one of ceramics selected from the group consisting of NiO, CoO, $Fe_3O_4$, MnO, $Bi_2O_3$, $Cr_2O_3$, $CrO_2$, AlN, $Al_2O_3$, $Cr_3C_2$, $BaTiO_3$, $Ti_2O_5$, $Ti_2O_3$, $SnO_2$, $ZrO_2$ and a combination thereof.

The life expectancy of ceramics may also be estimated from a variation in Young's modulus owing to the growth of grain in the ceramics in accordance with the thermal history. Ceramic members, to which such method may be applied, include those made of any one of ceramics selected from the group consisting of $Si_3N_4$, SiC, MgO, $ZrB_2$, SiAlON, $TiB_2$, TiN, $Al_6Si_2O_{13}$, BN, AlN, TiC, CrC, $Cr_3C_2$, $B_4C$, $ZrO_2$, $Al_2O_3$, and a combination thereof.

The estimation of the life expectancy of ceramic members according to the present invention is achieved on the basis of the growth of grain occurred in ceramics due to the thermal history thereof. The grain growth will cause a variation in grain size, electroconductivity, Young's modulus, and porosity.

The method of estimating the life expectancy of ceramics from a variation in color may be conducted by applying a specific element or a compound containing it (a color developer) to the ceramics to produce the colored ceramics and detecting the variation in color due to the thermal history the ceramics have undergone. In any case, the life expectancy of ceramic members can be easily estimated without fracturing the members as well as without requiring extensive hand labor.

The method of estimating the life expectancy of ceramic members according to the present invention will be illustrated with reference to Examples.

EXAMPLE 1

As a substrate to be flame sprayed with ceramics, a specimen of 50 mm in diameter×10 mm in thickness of a Ni based alloy called Hastelloy X comprising by weight 22% Cr, 1.5% Co, 9% Mo, 19% Fe, 0.1% C and a reminder of Ni was used. The surfaces of the specimen were degreased, washed and then was coated with a CoNiCrAlY (MCrAlY) alloy having an excellent resistance to corrosion by a plasma assisted flame spraying method to form a coating layer of a thickness of 20 μm as a bonding layer. The plasma assisted flame spraying was accomplished at an output of 40 kW and at a partial pressure of oxygen of $10^{-3}$ in an Ar atmosphere of 200 Torrs.

Figure 1:
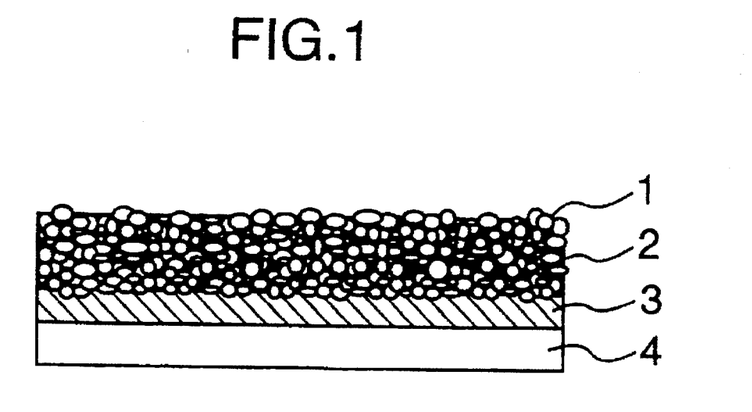
FIG. 1 is a schematic view of the structure of the $ZrO_2$ ceramic flame sprayed on a MCrAlY substrate.

Then a $ZrO_2$ coating layer containing 8% by weight $Y_2O_3$ was formed on the bonding layer to a thickness of 50 μm. The flame spraying was performed in air at an output of 50 kW. Thereafter, the specimen was heat-treated in vacuum at 1,060° C. for 10 hours to subject the aforementioned bonded layer and the substrate to diffusion treatment. A schematic cross-sectional view of the specimen is shown in FIG. 1. In FIG. 1, 1 denotes ceramic grains, 2 pores, 3 a MCrAlY where M is a metal, and 4 a Ni based alloy.

Figure 2:
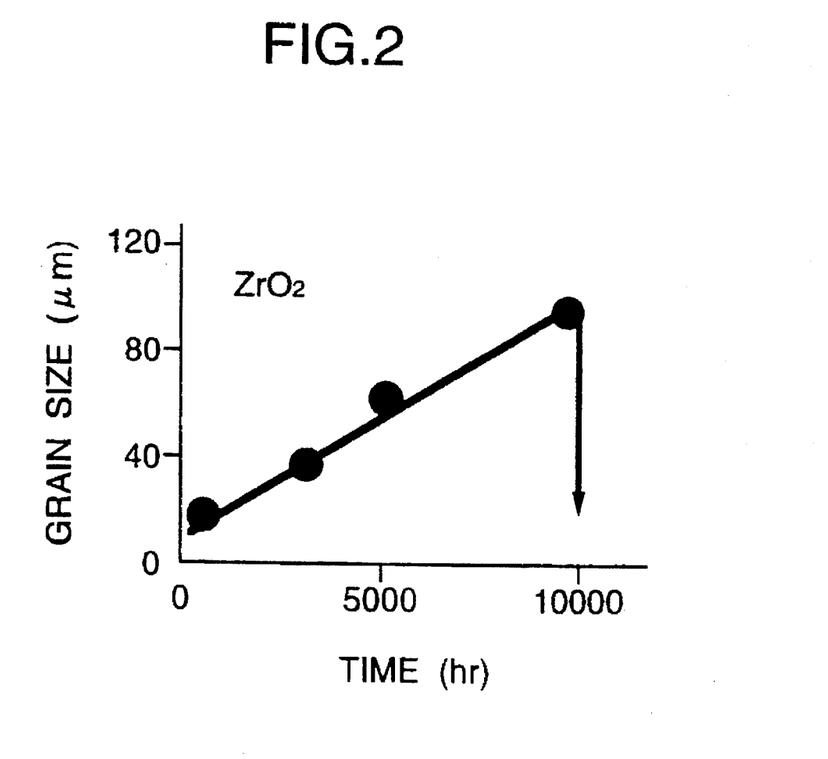
FIG. 2 shows a relationship between the average grain size of the $ZrO_2$ flame sprayed film and the retention time in air at 1,500° C.

The specimen was retained in air at 1,500° C. over an extended period of time to determine a relationship between the growth of grain (size of grain) and the retention time. The relationship between the average grain size and the retention time obtained for a $ZrO_2$ flame sprayed film is shown in FIG. 2.

Figure 3:
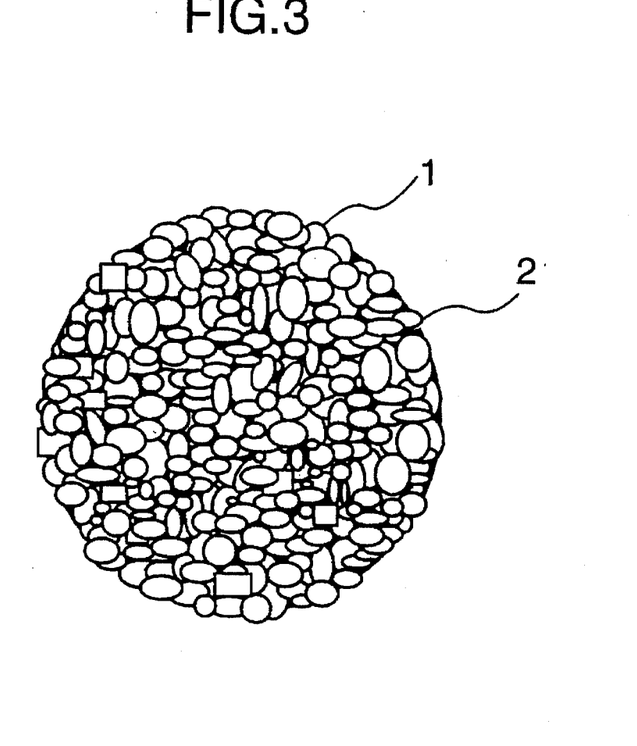
FIG. 3 is a schematic view of the structure of the $ZrO_2$ flame sprayed film before the grains grow.
Figure 4:
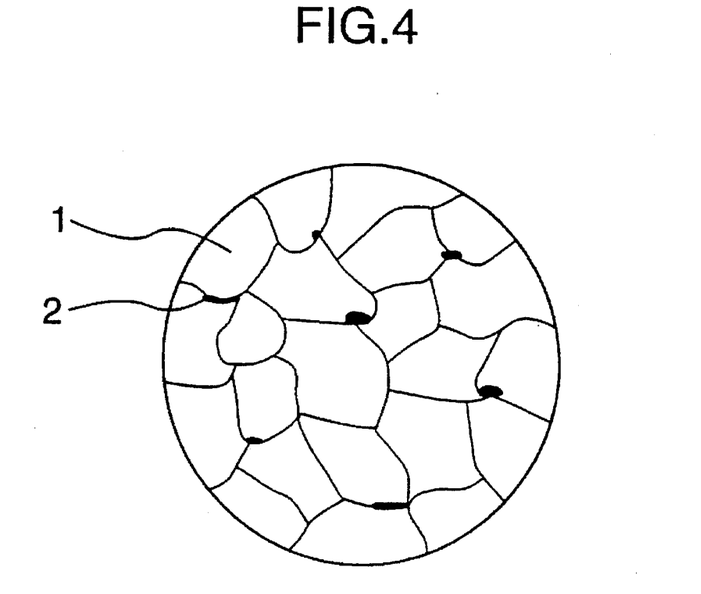
FIG. 4 is a schematic view of the structure of the $ZrO_2$ flame sprayed film after the grains have grown.

The specimen immediately after the flame spraying was effected had fine ceramic grains and a higher number of pores, but the grains grew and the pores were reduced with an increase in the retention time. The reduction in porosity may lead to a reduction in the ability of the flame sprayed film of relaxing thermal stresses. Therefore, the $ZrO_2$ flame sprayed films after retained for 10,000 hours were observed to have cracks and in times break apart and some could be easily flaked off by a slight shock. Thus the size of grain relates to the retention time. FIGS. 3 and 4 are schematic cross-sectional views of the structures of the flame sprayed film before and after the growth of grain was made. Like reference numerals refer to like parts in FIGS. 3 and 4.

Figure 5:
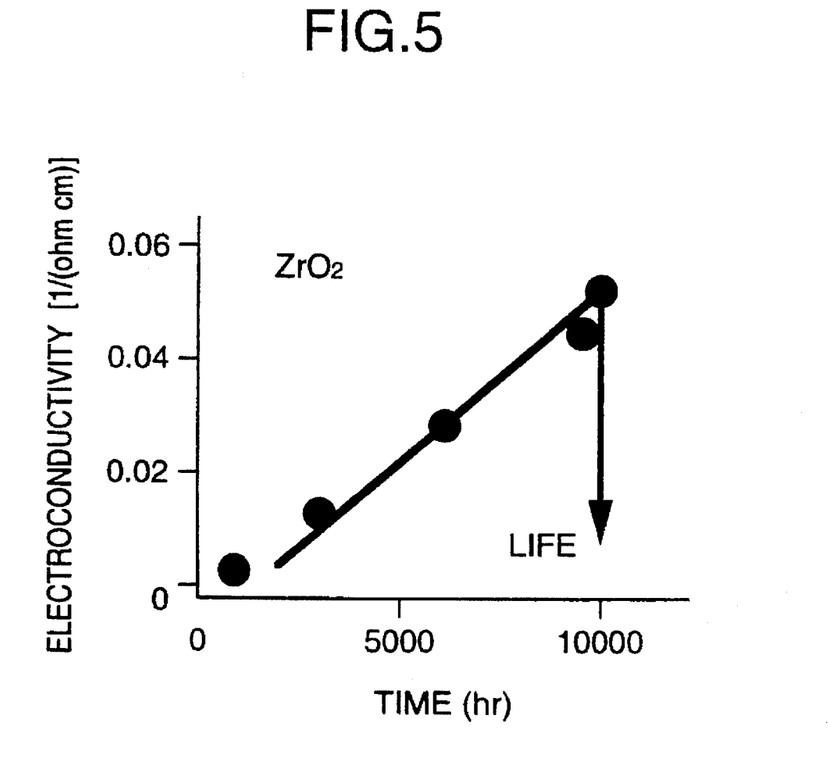
FIG. 5 shows a relationship between the electroconductivity and the retention time of the $ZrO_2$ flame sprayed.

For the flame sprayed films heated at 1,500° C. in air as described above the relationship between the retention time and the electroconductivity determined by a two terminal method is shown in FIG. 5.

The electroconductivity increased as the retention time was increased. It was found that the initial electroconductivity was 0.004 $\Omega^{-1}cm^{-1}$, while the electroconductivity after retained for 5,000 hours increased up to 0.007 $\Omega^{-1}cm^{-1}$. Moreover, for a retention time of 10,000 hours the electroconductivity increased up to 0.01 $\Omega^{-1}cm^{-1}$.

The electroconductivity of the flame sprayed films as described above varies with the retention time, hence with the size of grain. Therefore, it has been found that measurement of electroconductivity allows estimation of the life expectancy of ceramic members.

Similar experiments were made for other electroconductive oxide ceramic materials. The results are summarized in Table 1. The ceramics used were sintered preformed powder bodies and retained at sintering temperatures. Practicability of the measurement of electroconductivity for estimating the life expectancy of various ceramics are also summarized in the Table. The measurement of electroconductivity was made by using either two-, three-, or four-thermal method depending upon electroconducting mechanism and electroconductivity value.

TABLE 1

| 1  | NiO       | ○ |
|----|-----------|---|
| 2  | CoO       | ○ |
| 3  | $Fe_3O_4$ | Δ |
| 4  | MnO       | ○ |
| 5  | $Bi_2O_3$ | ○ |
| 6  | $Cr_2O_3$ | ○ |
| 7  | $CrO_2$   | ○ |
| 8  | AlN       | Δ |
| 9  | $Al_2O_3$ | ○ |
| 10 | $Cr_3C_2$ | ○ |
| 11 | $BaTiO_3$ | ○ |
| 12 | $Ti_2O_5$ | Δ |
| 13 | $Ti_2O_3$ | Δ |
| 14 | $SnO_2$   | ○ |

○: Dependency of the electroconductivity on the retention time was noticed and prediction of the growth of grain is possible.
Δ: Although dependency of the electroconductivity on the retention time was noticed, the prediction is not proctical.

Figure 6:
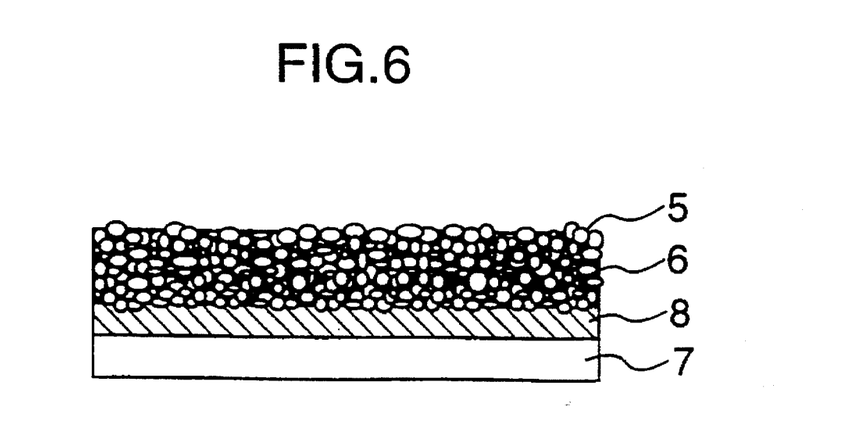
FIG. 6 is a schematic cross-sectional view of the surface of a turbine blade.

Taking account of the results of the experiments as described above, actual turbine blades were coated with $ZrO_2$ by a plasma assisted flame spraying method and operated on trial in a simulated plant to study the relationship between the electroconductivity and the operation time for the flame sprayed films. FIG. 6 shows a cross-sectional view of the surfaces of the turbine blades tested. In FIGS. 6, 5 denotes the catalyst, 6 the heat-shield coating layer, 7 the substrate and 8 the bonding layer.

Figure 7:
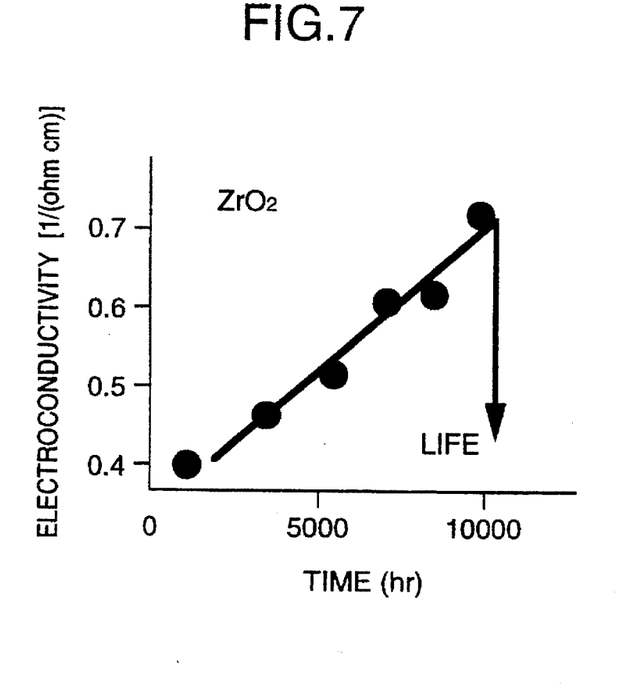
FIG. 7 shows a relationship between the electroconductivity and the retention time of the flame sprayed ceramic on the surface of a turbine blade.

As can be seen from FIG. 7, the relationship between the electroconductivity and the time was generally consistent with the results of the simulated tests as described above. A partly observed discrepancy seems to result from the deterioration of the blades owing to attack with impurities from exhaust gas, to which the gas turbine blades are exposed, and a wind pressure. After a total of retention time of 8,000 hours had elapsed, the flame sprayed films were observed to flake off.

EXAMPLE 2

Figure 8:
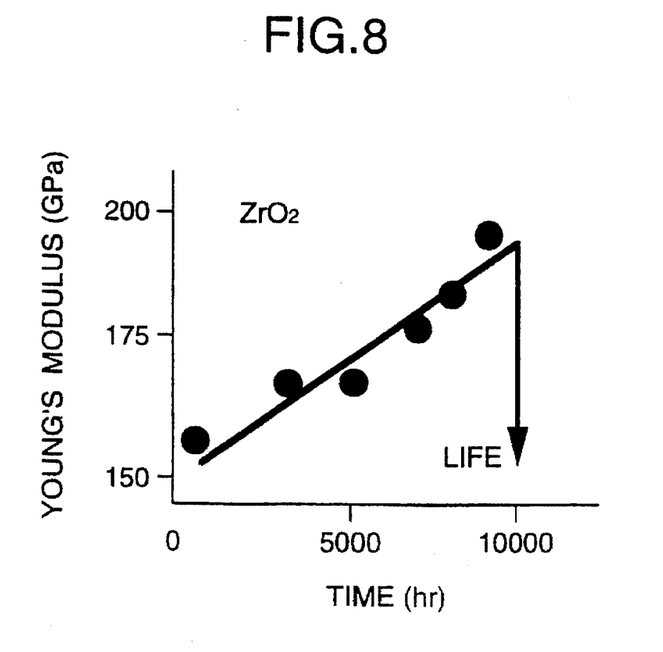
FIG. 8 shows a relationship between the Young's modulus and the retention time of the $ZrO_2$ flame sprayed film.

The same $ZrO_2$ flame sprayed films as those in Example 1 were tested in a procedure identical to that in Example 1 to determine the relationship between the retention time and the Young's modulus. The Young's modulus was measured as a function of time by a ultrasonic pulse method. The results are set forth in Table 8.

The initial Young's modulus was 160 GPa, while the Young's modulus was 172 GPa after retained for 5,000 hours and increased up to 195 GPa after retained for 10,000 hours. This increase in Young's modulus appears owing to densification of the $ZrO_2$ films, the grains of which had grown.

Figure 9:
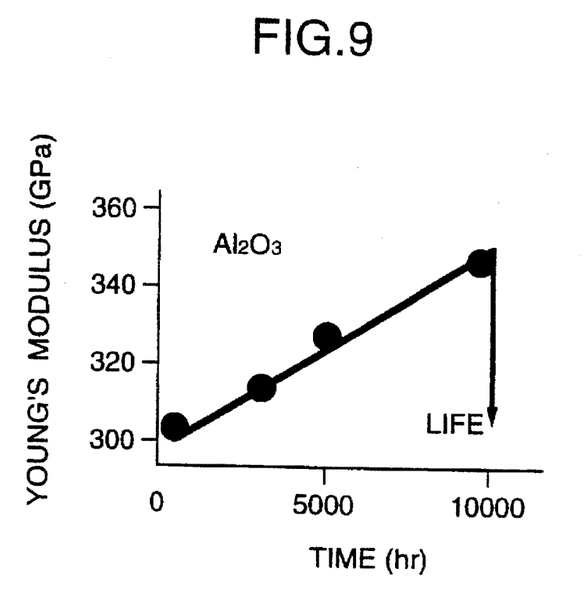
FIG. 9 shows a relationship between the Young's modulus and the retention time of the $Al_2O_3$ flame sprayed film.

Sintered $Al_2O_3$ preforms were retained in air at 1,500° C. in a manner identical to that in Example 1 to determine the relationship between the retention time and the Young's modulus. As can be seen from FIG. 9, the initial Young's modulus was 30 GPa, while the Young's modulus was 330 GPa after 5,000 hours and increased up to 350 GPa after retained for 10,000 hours.

Other ceramics were similarly tested at respective sintering temperatures. For all the ceramics applicability of Young's modulus to estimation of the life expectancy is summarized in Table 2.

TABLE 2

| 1  | $Si_3N_4$      | ○ |
|----|----------------|---|
| 2  | SiC            | ○ |
| 3  | MgO            | ○ |
| 4  | $ZrB_3$        | ○ |
| 5  | SiAlON         | ○ |
| 6  | $TiB_2$        | ○ |
| 7  | TiN            | ○ |
| 8  | $Al_4Si_2O_{13}$ | ○ |
| 9  | BN             | ○ |
| 10 | AlN            | ○ |
| 11 | TiC            | ○ |
| 12 | CrC            | ○ |
| 13 | $Cr_3C_2$      | ○ |
| 14 | $B_4C$         | ○ |
| 15 | $ZrO_2$        | ○ |
| 16 | $Al_2O_3$      | ○ |

○: Dependency of the Young's modulus on the retention time was noticed.

Figure 10:
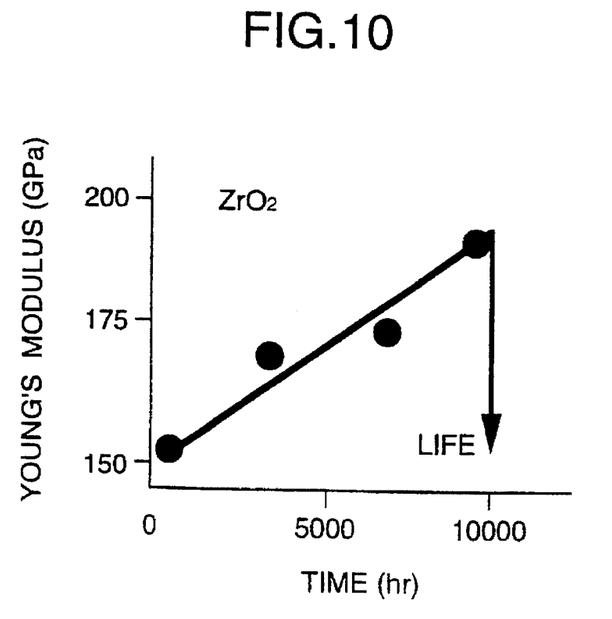
FIG. 10 shows a relationship between the Young's modulus and the retention time of the flame sprayed ceramic on the surface of a turbine blade.

Taking account of the results of the experiments as described above, actual turbine blades were coated with $ZrO_2$ by a plasma assisted flame spraying method and operated on trial in a simulated plant to study the relationship between the Young's modulus and the operation time for the flame sprayed films.

As can be seen from FIG. 10, the relationship between the Young's modulus and the time was consistent with the results as described above. After a retention time of 8,000 hours had elapsed, the flame sprayed films were observed to flake off.

EXAMPLE 3

A paste of $V_2O_5$ in ethyl alcohol in a ratio of $V_2O_5$ to ethyl alcohol of 80:20 by weight was coated on the end surface of a sintered $ZrO_2$ rod of 10 mm×10 mm×50 mm to a thickness of about 0.5 mm and maintained in air at 1,500° C. over an extended period of time to grow the grains, whereby the $V_2O_5$ was gradually diffused into the $ZrO_2$. One half of the specimen after 250 hours, and the overall specimen after 500 hours showed a color of H=5 Y, V=4, and C=4 according to JIS-Z-8721.

EXAMPLE 4

Figure 11:
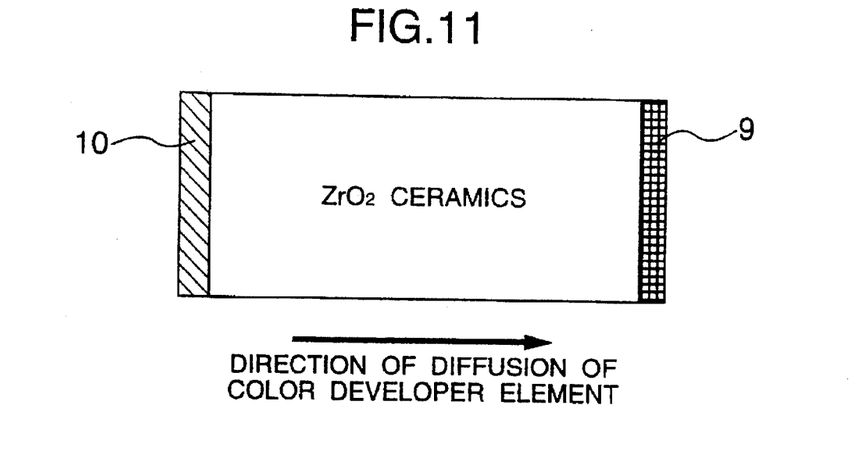
FIG. 11 is a schematic cross-sectional view of the ceramic when it was coated with a color developer.

One end portion in a length of a few centimeters from the edge of a $ZrO_2$ ceramic rod of 10 mm×10 mm×50 mm in a shape as shown in FIG. 11 was reacted with Si to converted into $ZrSiO_4$ and the other end surface was coated with a paste of a mixture of compounds containing V, Fe and Pr, respectively, i.e. $V_2O_5$, $Fe_2O_3$ and $Pr_2O_3$ in ethyl alcohol in a ratio of ethyl alcohol: $V_2O_5$:$Fe_2O_3$:$Pr_2O_3$=2:3:3:3 by weight in a thickness of about 0.5 mm. The rod was maintained in air at 1,500° C. over an extended period of time to grow the grains.

Owing to the diffusion of V, the $ZrSiO_4$ portion after about 500 hours showed a color of H=10BG, V=4, and C=2 according to JIS-Z-8721 and after about 550 hours the $ZrSiO_4$ portion appeared red in color due to the diffusion of Fe causing a color change into a color of H=2.5P, V=3, and C=2 according to JIS-Z-8721. Furthermore, after about 800 hours the $ZrSiO_4$ portion was yellow in color due to the diffusion of Pr showing a color of H=5YR, V=2, and C=2 according to JIS-Z-8721. In FIG. 11, 9 denotes the $ZrSiO_4$ portion and 10 denotes the portion coated with the color developers.

EXAMPLE 5

Ceramic coating layers formed by a CVD method were tested for estimation of the life expectancy similarly to the above Examples.

Figure 12:
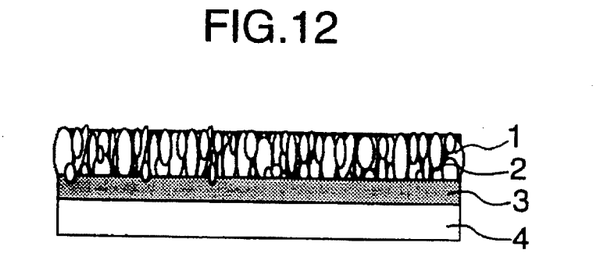
FIG. 12 is a schematic view of the structure of the ceramic coating layer formed by a CVD.

As a substrate a specimen of 50 mm in diameter×10 mm in thickness of the Ni based alloy called Hastelloy X identical to that in Example 1 was used. The surfaces of the specimen were degreased, washed and then was coated with a CoNiCrAlY (MCrAlY) alloy by a CVD method to form a bonding layer of a thickness of 10 μm. Then a $ZrO_2$ coating layer containing 8% by weight $Y_2O_3$ was formed on the surface of the bonding layer to a thickness of 30 μm. The CVD flame spraying was performed in air at an output of 50 kW. In FIGS. 12 and 1, similar reference numbers refer to similar parts.

Figure 13:
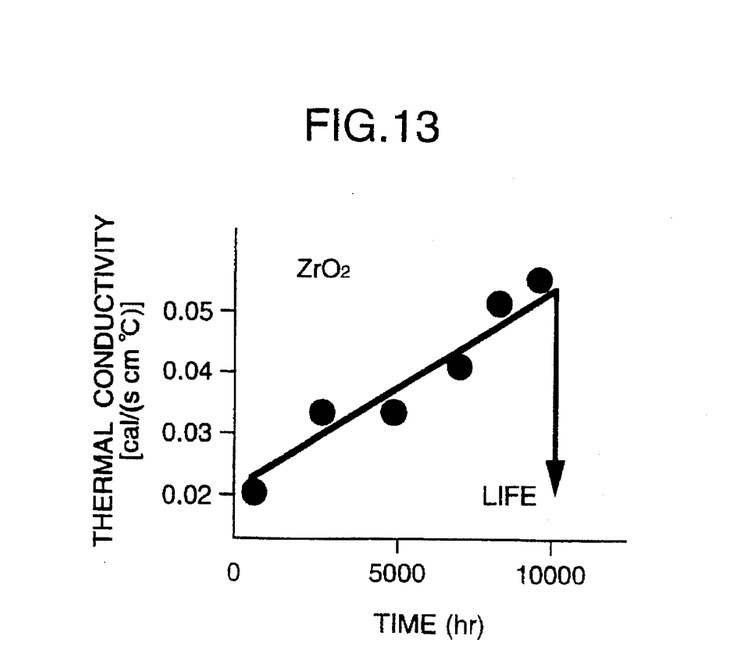
FIG. 13 shows a relationship between the electroconductivity and the retention time of the ceramic coating layer formed by a CVD.

The specimen obtained as above was retained in air at 1,500° C. over an extended period of time to determine a relationship between the retention time and the thermal conductivity. The results are represented in Table 13.

The electroconductivity increased as the retention time was increased showing the similar tendency to that in the case of the ceramic coating layer formed by the plasma assisted flame spraying method. It was found that the initial electroconductivity was 0.01 $\Omega^{-1}cm^{-1}$, while the electroconductivity after retained for 5,000 hours increased up to 0.012 $\Omega^{-1}cm^{-1}$. Moreover, after a retention time of 10,000 hours the electroconductivity increased up to 0.018 $\Omega^{-1}cm^{-1}$.

EXAMPLE 6

Figure 14:
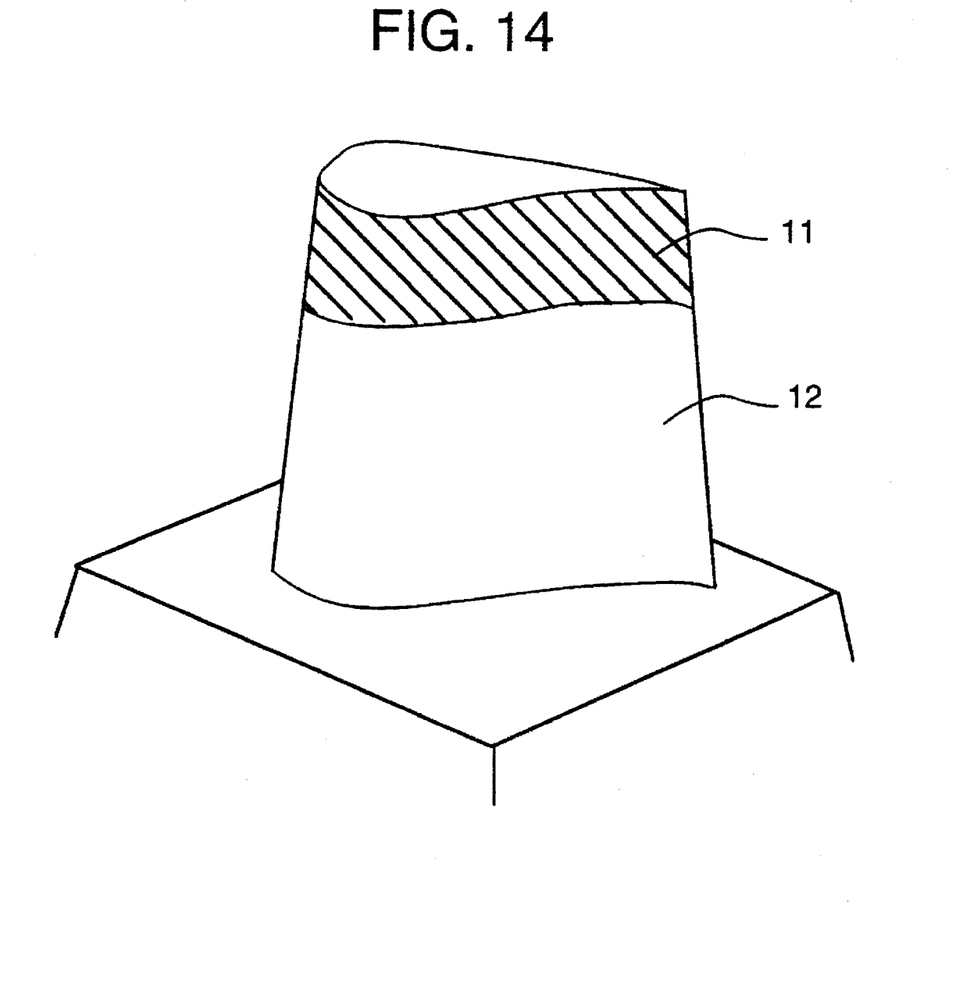
FIG. 14 is a schematic view of portions of a turbine blade, which are applied or flame sprayed with $Fe_2O_3$, $ZrO_2$, or $SiO_2$.
Figure 15:
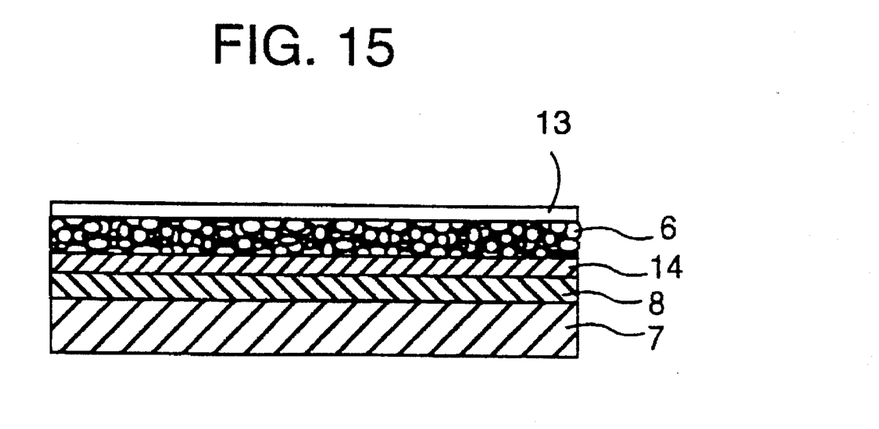
FIG. 15 is a schematic cross-sectional view of a color developed portion of a turbine blade.

A Ni substrate for turbine blades was partially coated with $Fe_2O_3$, and then $ZrO_2$ was flame sprayed on the substrate to form a film of a thickness of 0.5 mm as shown in FIG. 14. As shown in FIG. 15, $SiO_2$ was applied onto a portion of the $ZrO_2$ film, on the under surface of which the $Fe_2O_3$ was coated, and maintained in air at 1500° C. for 5 hours to convert the $SiO_2$ coated portion into $ZrSiO_4$ which was used as turbine blade in test.

Figure 16:
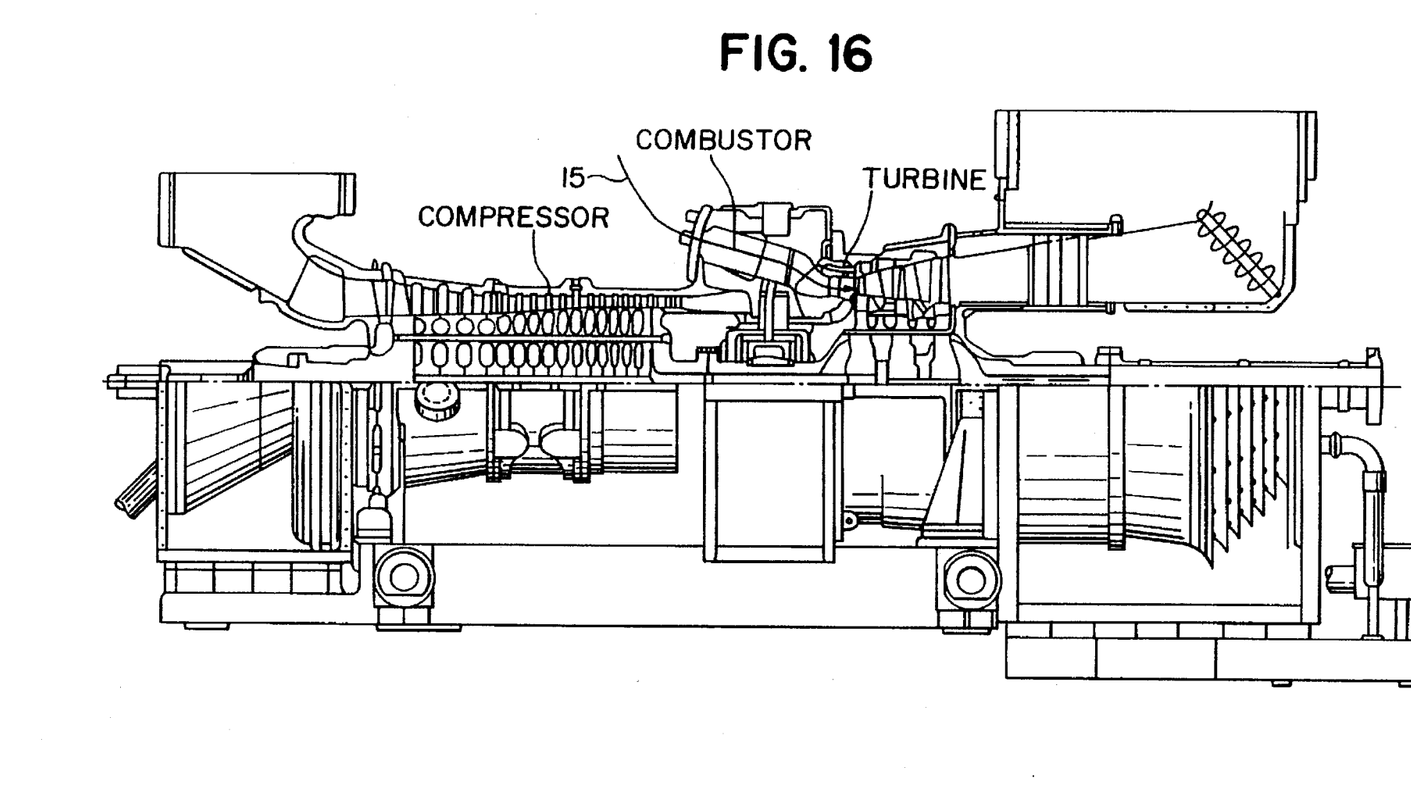
FIG. 16 is a schematic view of a fiber optics device inserted into a gas turbine apparatus of a generator in order to observe the turbine blades.

The turbine blades with the TBC coating film were attached in test on a gas turbine apparatus for a generator and operated in the conventional way. At the time of periodical inspection, a fiber optics device was inserted through a combustor liner port to observe with naked eyes the TBC coating film on the turbine blades as shown in FIG. 16. The turbine blades were operated intermittently at 1500° C. and inspected at a total operation time of 1,000, 5,000, and 10,000 hours. The inspection was made by observing the TBC coating film with the fiber optics device and then a part of the blade was sampled by partly fracturing the blade in the conventional manner to evaluate the fractured surfaces of the thermally resistant metal materials for the grain growth.

At a retention time of 5,000 hours, the fiber optics observation indicated that the $ZrSiO_4$ part of the blades was discolored in slightly pink color due to diffusion of $Fe_2O_3$ and the flame sprayed film underwent some cracks. At this point, the observation of the fractured surfaces of the thermally resistant metals and the calculation according to an A parameter method indicated a ratio of life expectancy of 0.65. At a retention time of 10,000 hours, the fiber optics observation indicated that the flame injected film was severely disrupted and the pattern was apparently colored in pink. A ratio of life expectancy was 1.28 according to the A parameter-method. This means that the turbine blades had been operated over about 120% of its life time. It can be appreciated, therefore that the observation of color by the fiber optics is in consistent with the observation of the fractured surfaces of the thermally resistant metals. Similarly the inspection of turbine blade was made by using a high sensitivity color sensor with a trichromatic LED of red, green and blue in color as a light source instead of the observation with naked eye. The information from the color sensor was processed to make a program based on the determination from the results of the naked eye observation and the length of time, during which the blades underwent thermal operation, was calculated. The results generally identical to those by the naked eye operation were obtained even though identification in color of the aggressively destroyed portions of the blades was inaccurate.

In FIGS. 14 to 16, reference number 11 denotes a part coated with a color developer element, 12 a part flame sprayed with $ZrO_2$, 13 $ZrSiO_4$, 14 a color developer element and 15 a fiber optics device.

As described above in detail, the method of estimating the life expectancy of ceramics according to the present invention allows easily the estimation of the life expectancy of materials to be inspected in a short time because it can be performed using physical qualities or color change which can be determined without fracturing the materials to be inspected. Particularly it is excellent in estimation of the life expectancy of the ceramic members used in gas turbine nuclear fusion reactor.

What is claimed is:

1. A method of estimating non-destructively a life expectancy of members, at least a surface layer of which is made of ceramics, comprising measuring a variation in at least one of physical qualities of said ceramics, and estimating the life expectancy of the members on a basis of a predetermined relationship between a life of said ceramics and variation in the at least one of the physical qualities.

2. A method of estimating non-destructively the life expectancy of members, at least a surface layer of which is made of ceramics, comprising measuring a variation in grain size due to the growth of grain in said surface layer and estimating the life expectancy of the ceramic members on the basis of the predetermined relationship between the life of said ceramics and the grain size.

3. The method of estimating non-destructively the life expectancy of ceramic members according to claim 1 or 2, wherein said ceramics are at least one selected from the group consisting of AlN, $Al_2O_3$, $Al_6Si_2O_{13}$, $B_4C$, $Bi_2O_3$, BN, $BaTiO_3$, CrC, $Cr_3C_2$, $Cr_2O_3$, $CrO_2$, CoO, $Fe_3O_4$, MnO, MgO, NiO, $Si_3N_4$, SiC, SAIALONE, $SnO_2$, $TiB_2$, TiN, TiC, $TiO_2$, $Ti_2O_5$, $Ti_2O_3$, $ZrB_2$, $ZrO_2$, and $ZrSiO_4$.

4. A method of estimating non-destructively the life expectancy of members, at least a surface layer of which is made of ceramics, comprising measuring a variation in electroconductivity of said members and estimating the life expectancy of the ceramic members on the basis of the predetermined relationship between the life of said ceramics and the electroconductivity.

5. The method of estimating non-destructively the life expectancy of ceramic members according to claim 4, wherein said ceramics are at least one selected from the group consisting of NiO, CoO, $Fe_3O_4$, MnO, $Bi_2O_3$, $Cr_2O_3$, $CrO_2$, AlN, $Al_2O_3$, $Cr_3C_2$, $BaTiO_3$, $Ti_2O_5$, $Ti_2O_3$, $SnO_2$, and $ZrO_2$.

6. A method of estimating non-destructively the life expectancy of members, at least a surface layer of which is made of ceramics, comprising measuring a variation in Young's modulus of said members and estimating the life expectancy of the ceramic members on the basis of the predetermined relationship between the life of said ceramics and the Young's modulus.

7. The method of estimating non-destructively the life expectancy of ceramic members according to claim 6, wherein said ceramics are at least one selected from the group consisting of $Si_3N_4$, SiC, MgO, $ZrB_2$, SAIALONE, $TiB_2$, TiN, $Al_6Si_2O_{13}$, BN, AlN, TiC, $Cr_3C_2$, CrC, $B_4C$, $ZrO_2$, and $Al_2O_3$.

8. A method of estimating non-destructively a life expectancy of members, at least a surface layer of which is made of ceramics, comprising measuring a variation in color of said members, and estimating the life expectancy of the members on a basis of a predetermined relationship between life of said ceramics and variation in the color.

9. The method of estimating non-destructively the life expectancy of members according to claim 8, wherein the at least one of color developers is added to the ceramics.

10. The method of estimating non-destructively the life expectancy of members according to claim 8, wherein the at least one of color developers is coated on the ceramics.

11. A method of estimating non-destructively a life expectancy of members, at least a surface layer of which is made of ceramics, comprising adding to or coating on the ceramics at least one of color developers, measuring a variation in color of said at least one of color developers, and estimating the life expectancy of the members on a basis of a predetermined relationship between life of said ceramics and variation in the color.

12. The method of estimating non-destructively the life expectancy of members according to claim 11, wherein the at least one of color developers is added to the ceramics.

13. The method of estimating non-destructively the life expectancy of members according to claim 11, wherein the at least one of color developers is coated on the ceramics.

14. The method of estimating non-destructively the life expectancy of members according to claim 11, wherein said color developers are selected from the group consisting of V, In, and Y+V in the case of $ZrO_2$ ceramics, or the group consisting of Co+Ni, CdS, Fe, Pr and V in the case of $ZrSiO_4$ ceramics, or the group consisting of V, Sb, Cr, and Ti in the case of $SnO_2$ ceramics, or the group consisting of Cr+Sb and W+Sb in the case of $TiO_2$ ceramics, or the group consisting of Mn, P and Cr in the case of $\alpha-Al_2O_3$ ceramics, or the group consisting of N+P and B+Al in the case of high purity SiC ceramics.

15. A method of estimating non-destructively the life expectancy of a gas turbine equipped with nozzles, blades and burners, at least one of which has a TBC (Thermal Barrier Coating) made of ceramics, comprising measuring a variation in at least one of characteristics of the ceramic grain size, electroconductivity and Young's modulus and estimating the life expectancy of the TBC on the basis of the predetermined relationship between the life of said ceramics and said characteristics.

16. A method of estimating non-destructively a life expectancy of a gas turbine equipped with nozzles, blades and burners, at least a portion of at least one of which has a Thermal Barrier Coating made of ceramics, to which a color developer is added or applied, comprising measuring a variation in color of the Thermal Barrier Coating, to which said color developer was added or applied, and estimating the life expectancy of the Thermal Barrier Coating made of said ceramics on a basis of a predetermined relationship between a life of said ceramics and variation in said color.

17. The method of estimating non-destructively the life expectancy of a gas turbine according to claim 16, wherein the Thermal Barrier Coating has said color developer added thereto.

18. The method of estimating non-destructively the life expectancy of a gas turbine according to claim 16, wherein the Thermal Barrier coating has the color developer applied thereon.

19. A method of estimating non-destructively the life expectancy of a nuclear fusion reactor, the wall surfaces of which are made of ceramics, comprising measuring a variation in at least one of characteristics of the grain size, electroconductivity and Young's modulus of said ceramic wall surfaces and estimating the life expectancy of said ceramic reactor wall on the basis of the predetermined relationship between the life of said ceramics and said characteristics.

20. A method of estimating non-destructively a life expectancy of wall surfaces of a nuclear fusion reactor, at least a portion of the wall surfaces of said nuclear fusion reactor being made of ceramics, to which a color developer is added or applied, comprising measuring a variation in color of the ceramics of the at least a portion, to which said color developer was added or applied, and estimating the life expectancy of said wall surfaces on a basis of a predetermined relationship between life of said ceramics and variation in said color.

21. The method of estimating non-destructively the life expectancy of wall surfaces of a nuclear fuel reactor according to claim 20, wherein said at least a portion of wall surfaces of said nuclear fusion reactor has said color developer added thereto.

22. The method of estimating non-destructively the life expectancy of wall surfaces of a nuclear fuel reactor according to claim 20, wherein said at least a portion of wall surfaces of said nuclear fusion reactor has said color developer applied thereon.

* * * * *